(12) United States Patent
Jang et al.

(10) Patent No.: US 10,202,407 B2
(45) Date of Patent: Feb. 12, 2019

(54) TRISILYL AMINE DERIVATIVE, METHOD FOR PREPARING THE SAME AND SILICON-CONTAINING THIN FILM USING THE SAME

(71) Applicant: DNF CO.,LTD., Daejeon (KR)

(72) Inventors: Se Jin Jang, Daegu (KR); Sang-Do Lee, Daejeon (KR); Jong Hyun Kim, Daejeon (KR); Sung Gi Kim, Daejeon (KR); Do Yeon Kim, Gyeongsangbuk-do (KR); Byeong-il Yang, Daejeon (KR); Jang Hyeon Seok, Daejeon (KR); Sang Ick Lee, Daejeon (KR); Myong Woon Kim, Daejeon (KR)

(73) Assignee: DNF CO.,LTD., Daejeon (KR)

( * ) Notice: Subject to any disclaimer, the term of this patent is extended or adjusted under 35 U.S.C. 154(b) by 0 days.

(21) Appl. No.: 15/110,692

(22) PCT Filed: Jan. 8, 2015

(86) PCT No.: PCT/KR2015/000168
§ 371 (c)(1),
(2) Date: Jul. 8, 2016

(87) PCT Pub. No.: WO2015/105337
PCT Pub. Date: Jul. 16, 2015

(65) Prior Publication Data
US 2016/0333030 A1 Nov. 17, 2016

(30) Foreign Application Priority Data

Jan. 8, 2014 (KR) .................. 10-2014-0002538
Dec. 30, 2014 (KR) .................. 10-2014-0193165

(51) Int. Cl.
| | | |
|---|---|---|
| C07F 7/10 | (2006.01) |
| C23C 16/40 | (2006.01) |
| C23C 16/455 | (2006.01) |
| H01L 21/02 | (2006.01) |

(52) U.S. Cl.
CPC .............. *C07F 7/10* (2013.01); *C23C 16/402* (2013.01); *C23C 16/45536* (2013.01); *C23C 16/45553* (2013.01); *H01L 21/0217* (2013.01); *H01L 21/0228* (2013.01); *H01L 21/02164* (2013.01); *H01L 21/02219* (2013.01); *H01L 21/02274* (2013.01)

(58) Field of Classification Search
CPC ... C07F 7/10; C23C 16/402; C23C 16/45536; C23C 16/45553

USPC ........................................ 556/412
See application file for complete search history.

(56) References Cited

U.S. PATENT DOCUMENTS 3,408,379 A * 10/1968 McVannel ............... C07F 7/10
528/34
2002/0016084 A1  2/2002 Todd

FOREIGN PATENT DOCUMENTS

| JP | S6420973 A | 1/1989 |
| JP | H03122102 A | 5/1991 |
| JP | 2010066597 A | 3/2010 |
| KR | 1020070055898 A | 5/2007 |

OTHER PUBLICATIONS

Zapilko et al., J. Amer. Chem. Soc., 2006, 128:16266-16276.*
Pola et al., Appl. Organometal. Chem., 2006, 20:648-655.*
Zapilko et al., J. Amer. Chem. Soc., 2006, 128:16266-16276 (Year: 2006).*
Schneider, J. et al., "Reaktionen von Lithiumhydridosilylamiden RR'(H)Si—N(Li)R" mit Chlortrimethylsilan in Tetrahydrofuran und unpolaren Lösungsmitteln: N-Silylierung und/oder Cyclodisilazanbildung," Zeitschrift für anorganische und allgemeine Chemie, vol. 627, No. 12, Dec. 2001, Available Online Nov. 8, 2001, 14 pages. (English Abstract on p. 1, See also NPL 4, International Search Report Issued in Application No. PCT/KR2015/000168).
Pola, J. et al., "UV laser deposition of nanostructured Si/C/O/N/H from disilazane precursors and evolution to silicon oxycarbonitride," Applied Organometallic Chemistry, vol. 20, No. 10, Oct. 2006, Published Online Aug. 7, 2006, 9 pages.
Zapilko, C. et al., "Advanced Surface Functionalization of Periodic Mesoporous Silica: Kinetic Control by Trisilazane Reagents," Journal of the American Chemical Society, vol. 128, No. 50, Dec. 20, 2006, Published Online Nov. 29, 2006, 11 pages.
ISA Korean Intellectual Property Office, International Search Report Issued in Application No. PCT/KR2015/000168, Apr. 8, 2015, WIPO, 2 pages.
Japanese Patent Office, Office Action Issued in Application No. 2017194414, dated Jun. 5, 2018, 6 pages.

* cited by examiner

*Primary Examiner* — Clinton A Brooks
*Assistant Examiner* — Kofi Adzamli
(74) *Attorney, Agent, or Firm* — McCoy Russell LLP (57) ABSTRACT

Provided are a novel trisilyl amine derivative, a method for preparing the same, and a silicon-containing thin film using the same, wherein the trisilyl amine derivative, which is a compound having thermal stability, high volatility, and high reactivity and being present in a liquid state at room temperature and under pressure where handling is possible, may form a high purity silicon-containing thin film having excellent physical and electrical properties by various deposition methods.

12 Claims, 4 Drawing Sheets

TRISILYL AMINE DERIVATIVE, METHOD FOR PREPARING THE SAME AND SILICON-CONTAINING THIN FILM USING THE SAME

CROSS REFERENCE TO RELATED APPLICATIONS

The present application is a U.S. National Phase of International Patent Application Ser. No. PCT/KR2015/000168, entitled "NOVEL TRISILYL AMINE DERIVATIVE, METHOD FOR PREPARING THE SAME AND SILICON-CONTAINING THIN FILM USING THE SAME," filed on Jan. 8, 2015, which claims priority to Korean Patent Application No. 10-2014-0002538, filed on Jan. 8, 2014, and to Korean Patent Application No. 10-2014-0193165, filed on Dec. 30, 2014, the entire contents of each of which are hereby incorporated by reference for all purposes.

TECHNICAL FIELD

The present invention relates to a novel trisilyl amine derivative, a method for preparing the same, and a silicon-containing thin film using the same, and more particularly, to a novel trisilyl amine derivative having thermal stability and high volatility and being present in a liquid state at room temperature and under a pressure where handling is possible, a method for preparing the same, and a silicon-containing thin film using the same.

BACKGROUND ART

A silicon-containing thin film is manufactured in various shapes, such as a silicon film, a silicon oxide film, a silicon nitride film, a silicon carbonitride film, a silicon oxynitride film, and the like, by various deposition processes in a semiconductor field, and is variously applied to many fields.

In particular, the silicon oxide film and the silicon nitride film may function as an insulating film, a diffusion prevention film, a hard mask, an etching stop layer, a seed layer, a spacer, trench isolation, intermetallic dielectric material and a protective layer in manufacturing a device, due to significantly excellent block property and oxidation resistance.

Recently, a polycrystalline silicon thin film has been used for a thin film transistor (TFT), a solar cell, and the like, and therefore, the application field thereof has varied.

As a representative technology known for manufacturing a silicon-containing thin film, there are metal organic chemical vapor deposition (MOCVD) forming a film on a surface of a substrate by reacting a silicon precursor in a mixed gas form and a reactive gas, or forming a film by direct reaction on a surface, and atomic layer deposition (ALD) forming a film by physical or chemical adsorption of a silicon precursor in a gas form on a surface of a substrate, followed by sequential introduction of a reactive gas. In addition, various technologies for manufacturing a thin film such as low pressure chemical vapor deposition (LPCVD), plasma enhanced chemical vapor deposition (PECVD), plasma enhanced atomic layer deposition (PEALD) using plasma capable of being deposited at a low temperature, and the like, are applied to a next-generation semiconductor and a display device manufacturing process, thereby being used to form ultra-fine patterns and deposit ultra-thin film having uniform and excellent properties at a nano-sized thickness. Representative examples of a precursor used in forming a silicon-containing thin film as described in Korean Patent Laid-Open Publication No. KR 2007-0055898 include silanes, silane chlorides, amino silanes and alkoxysilanes, and more specifically, silane chlorides such as dichlorosilane ($SiH_2Cl_2$) and hexachlorodisilane ($Cl_3SiSiCl_3$) and trisilylamine ($N(SiH_3)_3$), bis-diethylaminosilane ($H_2Si(N(CH_2CH_3)_2)_2$) and di-isopropylaminosilane ($H_3SiN(i-C_3H_7)_2$), and the like, which are used in a mass production of a semiconductor and a display.

However, according to miniaturization of devices caused by ultra-high integration of the devices, an increase in an aspect ratio, and diversification of device material, a technology of forming an ultra-fine thin film having a uniform and thin thickness and excellent electrical properties at a desired low temperature has been demanded, and thus, a high temperature process at 600° C. or more, deterioration of step coverage, etching property, and physical and electrical properties of a thin film at the time of using the existing silicon precursor are emerging as an issue, and accordingly, excellent novel silicon precursor has been demanded to be developed.

DISCLOSURE

Technical Problem

An object of the present invention is to provide a novel trisilyl amine derivative.

In addition, another object of the present invention is to provide a novel trisilyl amine derivative which is a precursor compound for thin film deposition.

Further, another object of the present invention is to provide a method for preparing a trisilyl amine derivative.

In addition, another object of the present invention is to provide a composition for depositing a silicon-containing thin film, which includes the trisilyl amine derivative of the present invention, a method for manufacturing a silicon-containing thin film, and the silicon-containing thin film manufactured by using the trisilyl amine derivative of the present invention.

Technical Solution

In one general aspect, the present invention provides a novel trisilyl amine derivative capable of forming a silicon thin film having excellent cohesion, high deposition rate, and excellent physical and electrical properties even at a low temperature.

The novel trisilyl amine derivative of the present invention is represented by the following Chemical Formula 1:

[Chemical Formula 1]

in Chemical Formula 1,
$R^1$ and $R^2$ are each independently hydrogen, halogen, or (C1-C3)alkyl.

The trisilyl amine derivative represented by Chemical Formula 1 of the present invention is present in a liquid-state at room temperature and under atmospheric pressure, and has superior volatility and excellent reactivity, thereby allowing a thin film to be easily formed.

Preferably, in Chemical Formula 1, a case in which both of $R^1$ and $R^2$ are methyl is excluded, the reason is because when both of $R^1$ and $R^2$ are methyl in Chemical Formula 1, the trisilyl amine derivative is present in a liquid state at room temperature and under atmospheric pressure, but still has low reactivity. Meanwhile, the trisilyl amine derivative of the present invention, excluding a case in which both of $R^1$ and $R^2$ are methyl, is a liquid state compound having superior volatility and excellent reactivity, thereby allowing a thin film to be easily formed.

In addition, due to a $Si_3N$ triangular planar molecular structure having three silicon atoms coupled to central nitrogen atom, the trisilyl amine derivative of the present invention has high thermal stability and low activation energy to thereby have excellent reactivity, and does not generate non-volatile by-product, thereby allowing a silicon-containing thin film having high purity to be easily formed.

In order for the trisilyl amine derivative represented by Chemical Formula 1 according to an exemplary embodiment of the present invention to form a thin film having high thermal stability and reactivity and high purity, it is preferred that in Chemical Formula 1, $R^1$ and $R^2$ are each independently hydrogen, halogen, or methyl, provided that a case in which both of $R^1$ and $R^2$ are methyl is excluded.

The Chemical Formula 1 according to an exemplary embodiment of the present invention may be selected from the following compounds, but the present invention is not limited thereto:

In addition, the trisilyl amine derivative represented by Chemical Formula 1 of the present invention may be preferably used as a precursor compound for depositing a silicon-containing thin film.

In another general aspect, the present invention provides a method for preparing a trisilyl amine derivative represented by Chemical Formula 1, the method including: preparing the trisilyl amine derivative represented by the following Chemical Formula 1 by reacting a compound represented by the following Chemical Formula 3 with a compound represented by the following Chemical Formula 4 in the presence of a base represented by the following Chemical Formula 2 or (C1-C7)alkyllithium:

[Chemical Formula 1]

[Chemical Formula 2]
$N(R^3)(R^4)(R^5)$

[Chemical Formula 3]

[Chemical Formula 4]

in Chemical Formulas 1 to 4,
$R^1$ and $R^2$ are each independently hydrogen, halogen, or (C1-C3)alkyl;
$R^3$ to $R^5$ are each independently (C1-C7)alkyl, and
$X^1$ is halogen.

Preferably, in Chemical Formulas 1 to 4, a case in which both of $R^1$ and $R^2$ are methyl is excluded.

(C1-C7)alkyllithium according to an exemplary embodiment of the present invention is a compound where lithium is bonded to (C1-C7)alkyl, for example, methyllithium, tert-butyllithium, n-butyllithium, and the like, and preferably, n-butyllithium.

In another general aspect, the present invention provides a method for preparing a trisilyl amine derivative represented by the following Chemical Formula 1, the method including: preparing the trisilyl amine derivative represented by the following Chemical Formula 1 by reacting a metal hydride with a compound represented by the following Chemical Formula 5:

[Chemical Formula 1]

[Chemical Formula 5]

in Chemical Formula 1 or 5,
$R^1$ and $R^2$ are each independently hydrogen, halogen, or (C1-C3)alkyl; and
$X^2$ or $X^3$ is each independently hydrogen or halogen.

Preferably, in Chemical Formulas 1 or 5, a case in which both of $R^1$ and $R^2$ are methyl is excluded.

A metal in the metal hydride according to an exemplary embodiment of the present invention may be an alkali metal or an alkali earth metal, and preferably, lithium.

Solvents used in the preparation method of the present invention are not limited if they are not reacted with the starting material among general organic solvents, for example, may be at least one selected from the group consisting of normalhexane (n-hexane), cyclohexane, normalpentane (n-pentane), diethyl ether, toluene, tetrahydrofuran (THF), dichloromethane (DCM), and trichloromethane (chloroform).

A reaction temperature in the preparation method of the present invention is not limited if the temperature is used in a general organic synthesis; however, it may be varied depending on an amount of the reaction time, the reaction material, and the starting material, wherein the reaction needs to be finished after confirming that the starting material is completely consumed by NMR, GC, and the like. When the reaction is finished, the solvent may be removed by filtration, followed by simple distillation under reduced pressure, and then a desired material may be separated and refined by general methods such as fractional distillation, distillation under reduced pressure, and the like.

Further, in another general aspect, the present invention provides a composition for depositing a silicon-containing thin film, including the trisilyl amine derivative as described above, and a method for manufacturing a silicon-containing thin film manufactured by using the trisilyl amine derivative as described above.

The composition for depositing a silicon-containing thin film of the present invention may contain the trisilyl amine derivative as a precursor for thin film deposition, and the trisilyl amine derivative in the composition for depositing a silicon-containing thin film may have a content within the range which is recognizable by a person skilled in the art in consideration of film forming conditions, or thickness, properties, and the like, of the thin film.

In another general aspect, the present invention provides a silicon-containing thin film manufactured by using the trisilyl amine derivative as described above.

The silicon-containing thin film of the present invention may be manufactured by general methods, for example, metal organic chemical vapor deposition (MOCVD), atomic layer deposition (ALD), low pressure chemical vapor deposition (LPCVD), plasma enhanced chemical vapor deposition (PECVD), plasma enhanced atomic layer deposition (PEALD), and the like.

The trisilyl amine derivative of the present invention has low activation energy and high reactivity, and minimizes generation of non-volatile by-product, such that the silicon-containing thin film manufactured by using the trisilyl amine derivative of the present invention as a precursor may have high purity and excellent physical and electrical properties.

Advantageous Effects

The trisilyl amine derivative of the present invention has excellent thermal stability and high reactivity, such that the silicon-containing thin film manufactured by using the trisilyl amine derivative as a precursor may have high purity and significantly excellent physical and electrical properties.

In addition, the trisilyl amine derivative of the present invention may have high content of silicon and be present in a liquid state at room temperature and under atmospheric pressure to thereby be easily stored and handled, and may have high volatility and high reactivity to be rapidly and easily deposited, and it is possible to deposit a thin film having excellent cohesion and superior step coverage.

Further, the silicon-containing thin film manufactured by using the trisilyl amine derivative of the present invention as a precursor may have high purity and significantly excellent physical and electrical properties.

DESCRIPTION OF DRAWINGS

The above and other objects, features and advantages of the present invention will become apparent from the following description of preferred embodiments given in conjunction with the accompanying drawings, in which.

BEST MODE

Hereinafter, the present invention will be described in more detail with reference to the following exemplary embodiments. However, the following exemplary embodiments describe the present invention by way of example only but are not limited thereto.

The following Examples of all compounds were practiced under anhydrous and inert atmosphere using a glovebox or a Schlenk pipe, products were analyzed by $^1$H Nuclear Magnetic Resonance (NMR, 400 MHz Ultrashield, Buruker), thermogravimetric analysis (TGA, L81-II, LINSEIS) and gas chromatography (GC, 7890A, Agilent Technologies), thickness of deposited thin films were measured by an Ellipsometer (M2000D, Woollam), and components of the films were analyzed by infrared spectroscopy (IFS66V/S & Hyperion 3000, Bruker Optiks) and auger electron spectroscope (Microlab 350, Thermo Electron).

EXAMPLE 1

Synthesis of tetramethyl disilazane 80 g (0.84 mol) of chloro dimethyl silane $(CH_3)_2SiHCl$ and 400 ml of n-hexane were put into a 1000 mL flame-dried Schlenk flask and stirred under anhydrous and inert atmosphere, and was cooled to a temperature of −30° C. 72 g (4.23 mol) of ammonia ($NH_3$) was slowly added thereto while maintaining a temperature at −30° C. After the addition was completed, a temperature of the reaction solution was slowly raised to room temperature, and the reaction solution was stirred at room temperature for 6 hours. After the reaction solution was filtrated, a white ammonium ($NH_4Cl$) solid obtained by the filtration was removed to obtain a filtrate, and a solvent was removed from the filtrate under reduced pressure to obtain 50.73 g (0.38 mol) of tetramethyl disilazane $(((CH_3)_2SiH)_2NH)$ with a yield of 90%.

$^1$H NMR (in $C_6D_6$): δ 0.09 (d, 12H, $HN(HSi(CH_3)_2))_2$, 4.66 (m, 2H, $HN(HSi(CH_3)_2))_2$); Boiling Point 99° C.

EXAMPLE 2

Synthesis of bis-tetramethylsilyl dichlorosilyl amine 40 g (0.30 mol) of tetramethyl disilazane ((($CH_3$)$_2$SiH)$_2$NH) synthesized by Example 1 above and 100 ml of an organic solvent (n-hexane) were put into a 2000 mL flame-dried flask and stirred under anhydrous and inert atmosphere, and 92.85 g (0.30 mol) of 2.29M normal butyl lithium (n-$C_4H_9$Li) hexane ($C_6H_{14}$) solution was slowly added while maintaining a temperature at −15° C. After the addition was completed, a temperature of the reaction solution was slowly raised to room temperature, and the reaction solution was stirred for 6 hours and 150 ml of tetrahydrofuran (O($C_2H_2$)$_2$) was added thereto. 4.47 g (0.33 mol) of trichlorosilane ($SiHCl_3$) was slowly added to the reaction solution while maintaining a temperature at −20° C. After the addition was completed, a temperature of the reaction solution was slowly raised to 25° C. and the reaction solution was stirred for 8 hours while maintaining a temperature at 25° C. After the reaction was completed, the reaction mixture was filtrated, and a white solid obtained by the filtration was removed to obtain a filtrate, and a solvent was removed from the filtrate under reduced pressure to obtain 55.75 g (0.24 mol) of bis-tetramethylsilyl dichlorosilyl amine ((($CH_3$)$_2$HSi)$_2$NSiHCl$_2$) with a yield of 80%.

$^1$H-NMR (in $C_6D_6$): δ 0.17 (d, 12H, (($CH_3$)$_2$HSi)$_2$NSiHCl$_2$)), 4.64 (m, 2H, (($CH_3$)$_2$HSi)$_2$NSiHCl$_2$), 6.09 (s, 1H, (($CH_3$)$_2$HSi)$_2$NSiHCl$_2$).

EXAMPLE 3

Synthesis of bis-dimethylsilyl silyl amine 55.7 g (0.24 mol) of bis-tetramethylsilyl dichlorosilyl amine ((($CH_3$)$_2$HSi)$_2$NSiHCl$_2$) synthesized by Example 2 above and 200 ml of an organic solvent (THF) were put into a 2000 mL flame-dried flask and stirred under anhydrous and inert atmosphere, and cooled to a temperature of −15° C. 4.77 g (0.60 mol) of lithium hydride (LiH) was slowly added thereto while maintaining a temperature at −15° C. After the addition was completed, a temperature of the reaction solution was slowly raised to 65° C. and the reaction solution was stirred for 12 hours. After the reaction solution was filtrated, a white solid obtained by the filtration was removed to obtain a filtrate. A solvent was removed from the filtrate under reduced pressure to obtain 25.50 g (0.16 mol) of bis-dimethylsilyl silyl amine ((($CH_3$)$_2$HSi)$_2$NSiH$_3$) with a yield of 65% by distillation under reduced pressure.

$^1$H-NMR (in $C_6D_6$): δ 0.16 (d, 12H, ((($CH_3$)$_2$HSi)$_2$NSiH$_3$)), 4.49 (s, 3H, ((($CH_3$)$_2$HSi)$_2$NSiH$_3$)), 4.69 (m, 2H, ((($CH_3$)$_2$HSi)$_2$NSiH$_3$)); Boiling Point 115~120° C.; GC Analysis Result >99%.

EXAMPLE 4

Synthesis of tris-dimethylsilyl amine 40 g (0.30 mol) of tetramethyl disilazane ((($CH_3$)$_2$SiH)$_2$NH) synthesized by Example 1 above and 100 ml of an organic solvent (n-hexane) were put into a 2000 mL flame-dried flask and stirred under anhydrous and inert atmosphere, and 92.85 g (0.30 mol) of 2.29M normal butyl lithium (n-$C_4H_9$Li) hexane ($C_6H_{14}$) solution was slowly added while maintaining a temperature at −15° C. After the addition was completed, a temperature of the reaction solution was slowly raised to room temperature, and the reaction solution was stirred for 6 hours and 150 ml of tetrahydrofuran (O($C_2H_2$)$_2$) was added thereto. 31.22 g (0.33 mol) of chlorodimethylsilane (($CH_3$)$_2$SiHCl) was slowly added to the reaction solution while maintaining a temperature at −20° C. After the addition was completed, a temperature of the reaction solution was slowly raised to 25° C. and the reaction solution was stirred for 8 hours while maintaining a temperature at 25° C. After the reaction was completed, the reaction mixture was filtrated, and a white solid obtained by the filtration was removed to obtain a filtrate, and a solvent was removed from the filtrate under reduced pressure to obtain 45.96 g (0.24 mol) of tris-dimethylsilyl amine ((($CH_3$)$_2$HSi)$_3$N) with a yield of 80%.

$^1$H-NMR (in $C_6D_6$): δ 0.21 (d, 18H, ((($CH_3$)$_2$HSi)$_3$N), 4.73 (s, 3H, ((($CH_3$)$_2$HSi)$_3$N); Boiling Point 152° C.; GC Analysis Result >99.5%.

EXAMPLE 5

Figure 1:
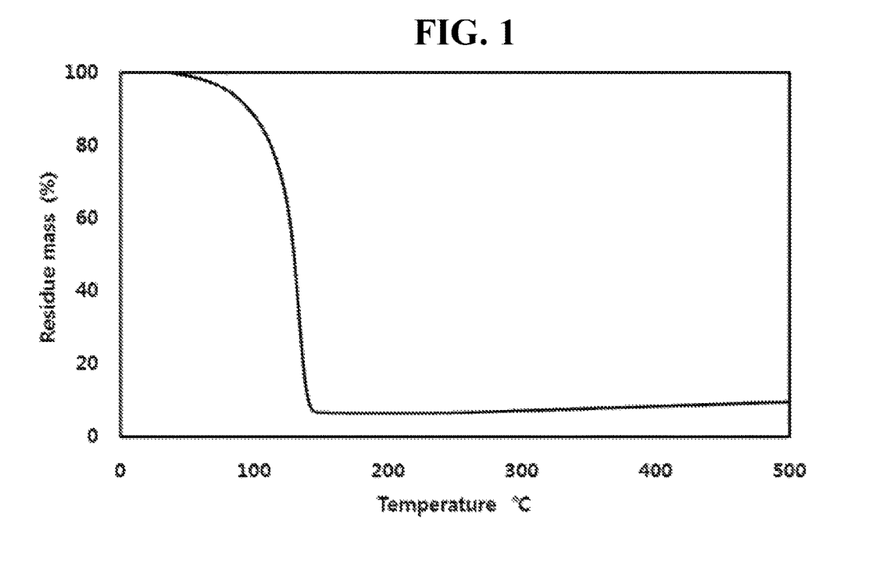
FIG. 1 shows a result obtained by thermogravimetric analysis of a trisilyl amine derivative prepared by Example 3.
Figure 2:
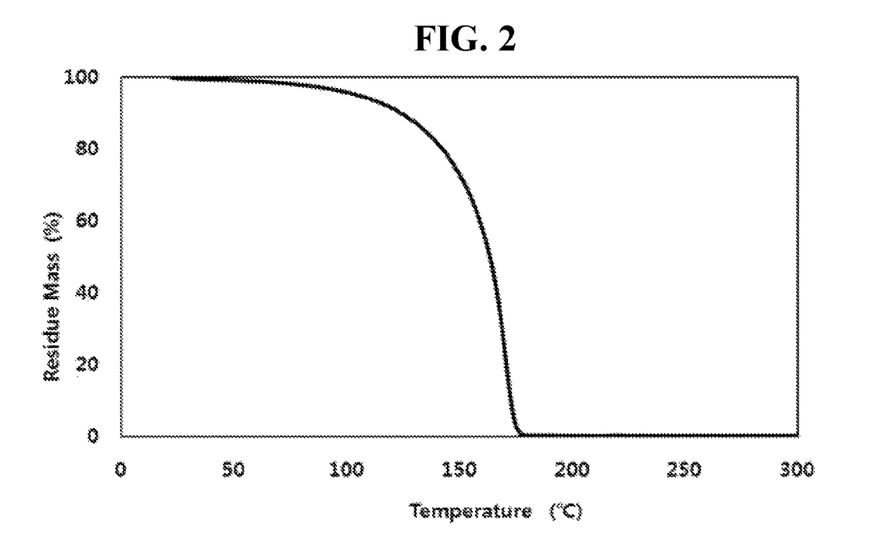
FIG. 2 shows a result obtained by thermogravimetric analysis of a trisilyl amine derivative prepared by Example 4.
Figure 3:
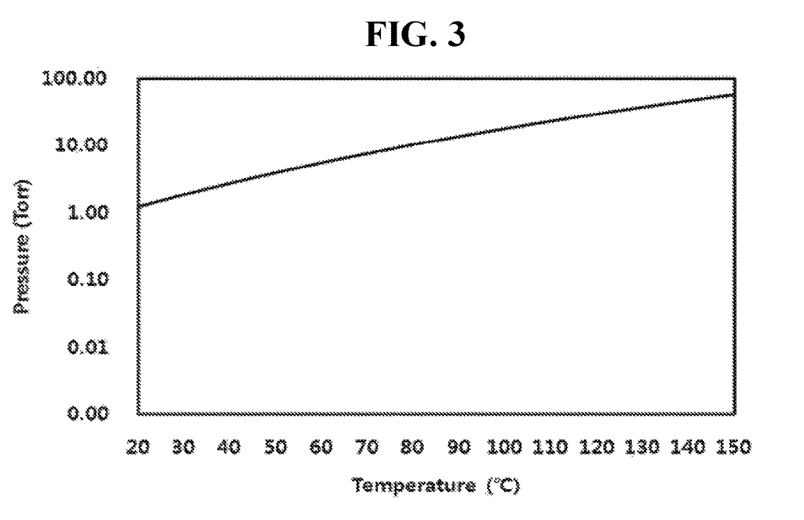
FIG. 3 shows a result obtained by vapor pressure measurement of the trisilyl amine derivative prepared by Example 4.
Figure 4:
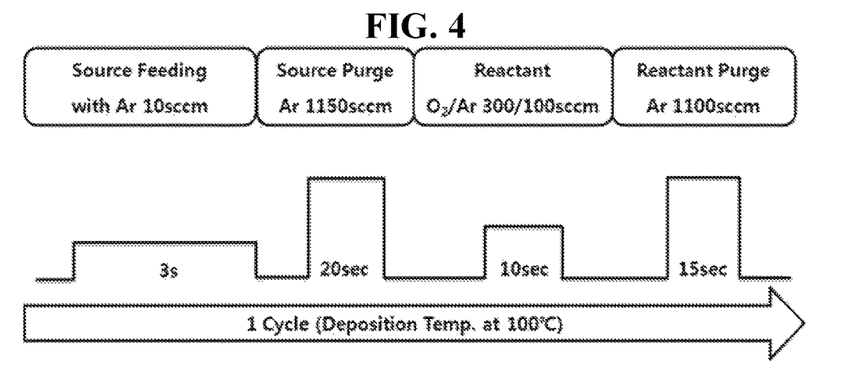
FIG. 4 shows a method for depositing a silicon-containing thin film practiced by Example 4.

Deposition of Silicon Oxide Film by Plasma Enhanced Atomic Layer Deposition (PEALD) Using Trisilyl Amine Derivative Film forming evaluation was conducted by using the trisilyl amine derivatives of Examples 3 and 4 according to the present invention as a composition for forming a silicon oxide film in a general plasma enhanced atomic layer deposition (PEALD) apparatus using the known PEALD method. Silicon substrate was used a substrate, oxygen together with plasma was used as a reaction gas, and argon which is an inert gas was used for purging. Hereinafter, FIG. 4 and Table 1 specifically show a method for depositing the silicon oxide thin film.

TABLE 1

| Deposition Condition of Silicon Oxide Thin film | | | |
|---|---|---|---|
| | | Precursor | |
| | | Bis-dimethylsilyl silyl amine | Tris-dimethylsilyl amine |
| Heating Temperature (° C.) of Precursor | | 5 | 35 |
| Substrate Temperature (° C.) | | 100 | 100 |
| Kind of Substrate | | Si wafer | Si wafer |
| Injection Time (sec) of Precursor | | 3 | 3 |
| Purge | Flow Amount (sccm) | 1100 | 1100 |
| | Time (sec) | 20 | 20 |
| 400W Oxygen Plasma | Flow Amount (sccm) of Oxygen/Argon | 300/100 | 300/100 |
| | Time (sec) | 10 | 10 |
| Purge | Flow Amount (sccm) | 1100 | 1100 |
| | Time (sec) | 15 | 15 |
| Frequency of Deposition | Cycle | 50 | 50 |

Figure 5:
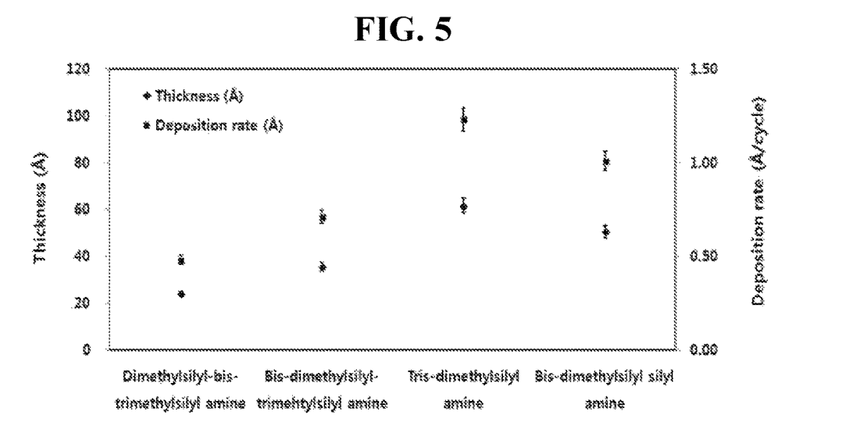
FIG. 5 shows a result obtained by analyzing a film thickness of a silicon-containing thin film manufactured by Example 5, using an Ellipsometer.
Figure 6:
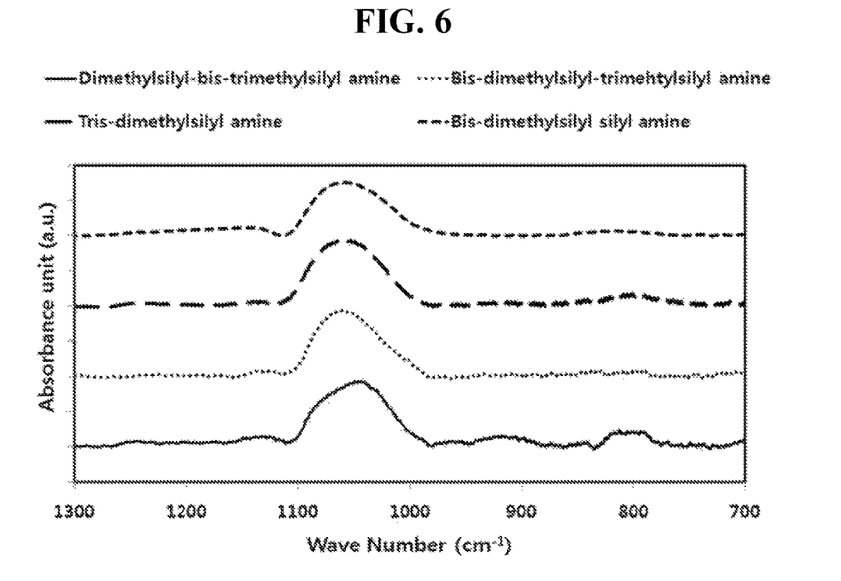
FIG. 6 shows a result obtained by infrared spectroscopic analysis of the deposited silicon-containing thin film manufactured by Example 5 (horizontal axis: wave number ($cm^{-1}$)).

A thickness of the deposited thin film was measured by an Ellipsometer, and formation of $SiO_2$ thin film was analyzed by infrared spectrophotometer. FIG. 5 shows a thickness of the film by Ellipsometer analysis. It was confirmed that a thickness of the thin film deposited by using the bis-dimethylsilyl silyl amine compound was 50.5 Å, and a thickness of the thin film deposited by using the tris-dimethylsilyl amine compound was 65.8 Å. It is determined that these thin films are capable of being effectively used throughout all silicon oxide thin film application fields requiring a high deposition rate. FIG. 6 shows infrared spectroscopic analysis of the deposited film. It was shown that all of the thin films were formed as silicon oxide thin films, and peak of impurities such as C—H, Si—OH was not observed.

That is, it was confirmed that the novel trisilyl amine derivative prepared by the present invention has high utilization value in forming a high purity silicon oxide thin film having a high deposition rate by plasma enhanced atomic layer deposition (PEALD).

COMPARATIVE EXAMPLE

Deposition of Silicon Oxide Film by Plasma Enhanced Atomic Layer Deposition (PEALD) Using Known Trisilyl Amine Derivative Film forming evaluation of Comparative Example was conducted by using a known PEALD method under the same deposition conditions as practiced by Example 5 above except for using known trisilyl amine derivative as shown in the following Table 2, then, the deposited thin film was analyzed by the same analysis method and conditions as practiced by Example 5 above, and the analysis result thereof was obtained. Hereinafter, FIG. 4 and Table 2 specifically show a method for depositing the silicon oxide thin film.

It was shown that the thin films had a thickness ranging from 21 to 35.5 Å, which showed a low deposition rate as compared to the trisilyl amine derivatives of Examples 3 and 4, and all thin films were formed as the silicon oxide film.

TABLE 2

Silicon Oxide Thin film Deposition Condition

| | | Precursor | |
|---|---|---|---|
| | | Dimethylsilyl-bis-trimethylsilyl amine | Bis-dimethylsilyl-trimethylsilyl amine |
| Heating Temperature (° C.) of Precursor | | 40 | 40 |
| Substrate Temperature (° C.) | | 100 | 100 |
| Kind of Substrate | | Si wafer | Si wafer |
| Injection Time (sec) of Precursor | | 1 | 1 |
| Purge | Flow Amount (sccm) | 1100 | 1100 |
| | Time (sec) | 20 | 20 |
| 400W Oxygen Plasma | Flow Amount (sccm) of Oxygen/Argon | 300/100 | 300/100 |
| | Time (sec) | 10 | 10 |
| Purge | Flow Amount (sccm) | 1100 | 1100 |
| | Time (sec) | 15 | 15 |
| Frequency of Deposition | Cycle | 50 | 50 |

EXAMPLE 6

Figure 7:
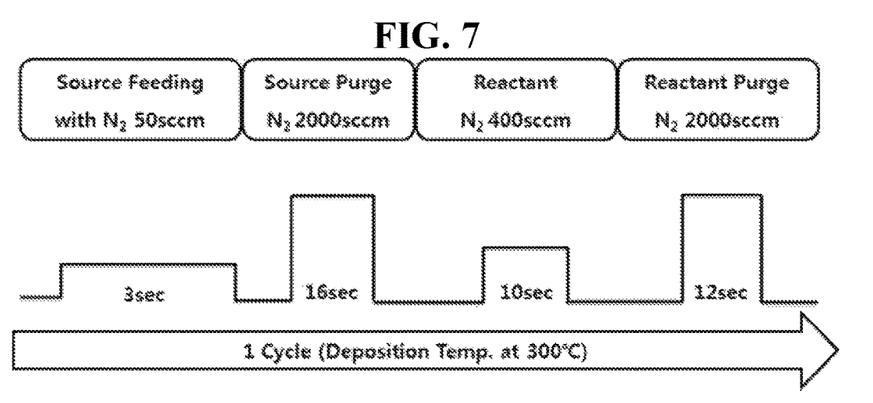
FIG. 7 shows a method for depositing a silicon-containing thin film practiced by Example 6.

Deposition of Silicon Nitride Film by Plasma Enhanced Atomic Layer Deposition (PEALD) Using Trisilyl Amine Derivative Film forming evaluation was conducted by using the trisilyl amine derivative of Example 3 according to the present invention as a composition for forming a silicon nitride film in a general plasma enhanced atomic layer deposition (PEALD) apparatus using the known PEALD method. Silicon substrate was used a substrate, nitrogen together with plasma was used as a reaction gas, and the same nitrogen gas was used for purging. Hereinafter, FIG. 7 and Table 3 specifically show a method for depositing the silicon nitride thin film.

TABLE 3

Deposition Condition of Silicon Nitride Thin film

| | | Precursor Bis-dimethylsilyl silyl amine |
|---|---|---|
| Heating Temperature (° C.) of Precursor | | 40 |
| Substrate Temperature (° C.) | | 300 |
| Kind of Substrate | | Si wafer |
| Injection Time (sec) of Precursor | | 5 |
| Purge | Flow Amount (sccm) | 2000 |
| | Time (sec) | 16 |
| 100W Nitrogen Plasma | Flow Amount (sccm) of Nitrogen | 400 |
| | Time (sec) | 10 |
| Purge | Flow Amount (sccm) | 2000 |
| | Time (sec) | 12 |
| Frequency of Deposition | Cycle | 500 |

A thickness of the deposited thin film was measured by an Ellipsometer, and formation of SiN thin film and components of the thin film were analyzed by an infrared spectrophotometer and an auger electron spectrometer. In 500 cycles on a flat panel wafer, a thickness of the thin film was 130.1 Å.

Figure 8:
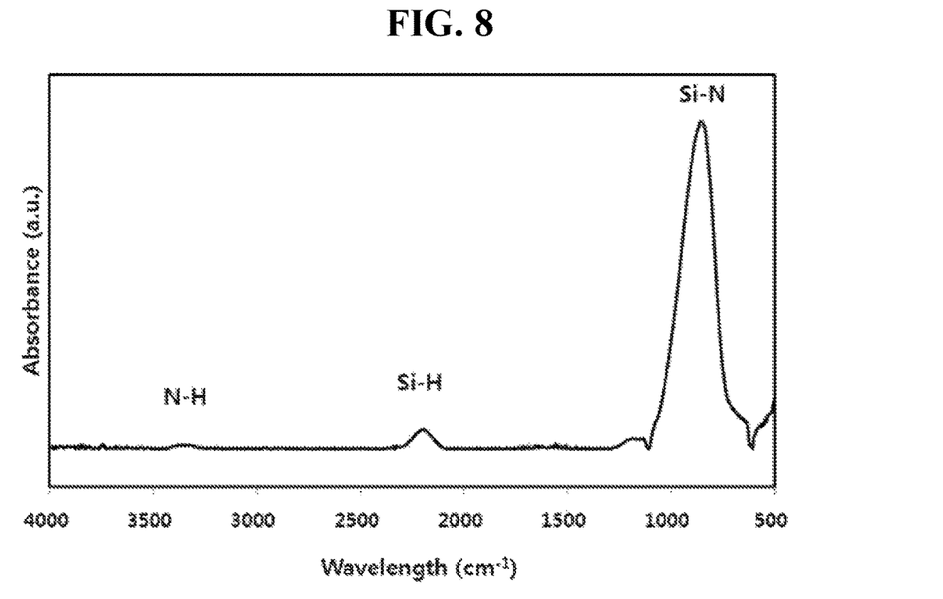
FIG. 8 shows a result obtained by infrared spectroscopic analysis of the silicon-containing thin film practiced by Example 6.

In addition, as shown in FIG. 8, it was shown that all of the deposited thin films were formed as silicon nitride films, and it was observed that a small number of bonds such as N—H, Si—H were included.

In addition, an etch rate of the deposited thin film was confirmed by using buffered oxide etchant (BOE) solution (300:1). The deposited silicon nitride thin film was etched at a rate of 0.04 Å/sec, and a silicon oxide thin film (thermal oxide) deposited by a pyrolysis deposition method at 1000° C. as a comparative sample was etched at a rate of 0.34 Å/sec, and a silicon nitride thin film deposited by low pressure chemical vapor deposition (LPCVD) at 770° C. using dichloro silane was etched at a rate of 0.02 Å/sec.

That is, it was confirmed that the novel trisilyl amine derivative prepared by the present invention has high utilization value in forming a high purity silicon nitride thin film having a high deposition rate and excellent etch resistance by plasma enhanced atomic layer deposition (PEALD).

The invention claimed is:

1. A trisilyl amine derivative represented by the following Chemical Formula 1:

[Chemical Formula 1]

in Chemical Formula 1,
R$^1$ and R$^2$ are each independently hydrogen, or (C1- C3) alkyl, excluding a case in which both of R$^1$ and R$^2$ are methyl.

2. The trisilyl amine derivative of claim 1, wherein the Chemical Formula 1 is selected from the following compounds:

3. A method for preparing a trisilyl amine derivative represented by the following Chemical Formula 1 of claim 1, comprising:
preparing the trisilyl amine derivative represented by the following Chemical Formula 1 of claim 1 by reacting a compound represented by the following Chemical Formula 3 with a compound represented by the following Chemical Formula 4 in the presence of a base represented by the following Chemical Formula 2 or (C1-C7)alkyllithium:

in Chemical Formulas 1 to 4,
R$^1$ and R$^2$ are each independently hydrogen, or (C1-C3)alkyl, excluding a case in which both of R$^1$ and R$^2$ are methyl;
R$^3$ to R$^5$ are each independently (C1-C7)alkyl, and
X$^1$ is halogen.

4. A method for preparing a trisilyl amine derivative represented by the following Chemical Formula 1 of claim 1, the method comprising:
preparing the trisilyl amine derivative represented by the following Chemical Formula 1 of claim 1 by reacting a metal hydride with a compound represented by the following Chemical Formula 5:

[Chemical Formula 1]

[Chemical Formula 5]

in Chemical Formula 1 or 5,
R$^1$ and R$^2$ are each independently hydrogen, or (C1-C3) alkyl, excluding a case in which both of R$^1$ and R$^2$ are methyl; and
X$^2$ or X$^3$ is each independently hydrogen or halogen.

5. A composition for depositing a silicon-containing thin film, comprising the trisilyl amine derivative of claim 1.

6. A method for manufacturing a silicon-containing thin film by using the composition for depositing a silicon-containing thin film of claim 5.

7. A trisilyl amine derivative represented by the following Chemical Formula 1:

[Chemical Formula 1]

in Chemical Formula 1,
R$^1$ and R$^2$ are each independently hydrogen, halogen, or (C2-C3) alkyl.

8. The trisilyl amine derivative of claim 7, wherein the Chemical Formula 1 is selected from the following compounds:

9. A composition for depositing a silicon-containing thin film, comprising the trisilyl amine derivative of claim 7.

10. A method for manufacturing a silicon-containing thin film by using the composition for depositing a silicon-containing thin film of claim 9.

11. A method for preparing a trisilyl amine derivative represented by the following Chemical Formula 1 of claim 7, comprising:
preparing the trisilyl amine derivative represented by the following Chemical Formula 1 of claim 7 by reacting a compound represented by the following Chemical Formula 3 with a compound represented by the following Chemical Formula 4 in the presence of a base represented by the following Chemical Formula 2 or (C1-C7)alkyllithium:

[Chemical Formula 1]

[Chemical Formula 2]

[Chemical Formula 3]

[Chemical Formula 4]

in Chemical Formulas 1 to 4,
R$^1$ and R$^2$ are each independently hydrogen, halogen, or (C2-C3)alkyl;
R$^3$ to R$^5$ are each independently (C1-C7)alkyl, and
X$^1$ is halogen.

12. A method for preparing a trisilyl amine derivative represented by the following Chemical Formula 1 of claim 7, the method comprising:
preparing the trisilyl amine derivative represented by the following Chemical Formula 1 of claim 7 by reacting a metal hydride with a compound represented by the following Chemical Formula 5:

[Chemical Formula 1]

[Chemical Formula 5]

in Chemical Formula 1 or 5,
R$^1$ and R$^2$ are each independently hydrogen, halogen, or (C2-C3)alkyl; and
X$^2$ or X$^3$ is each independently hydrogen or halogen.

* * * * *